(12) United States Patent
Qiu et al.

(10) Patent No.: US 11,237,144 B2
(45) Date of Patent: Feb. 1, 2022

(54) USING RESISTIVITY MEASUREMENTS TO MONITOR THE REACTION KINETICS BETWEEN ACIDS AND CARBONATE ROCKS

(71) Applicant: SCHLUMBERGER TECHNOLOGY CORPORATION, Sugar Land, TX (US)

(72) Inventors: Xiangdong Qiu, Al-Khobar (SA); Abdul Muqtadir Mohammed, Al Khobar (SA); Mustapha Abbad, Al-Khobar (SA); Reza Taherian, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 412 days.

(21) Appl. No.: 15/946,729

(22) Filed: Apr. 5, 2018

(65) Prior Publication Data
US 2019/0310237 A1 Oct. 10, 2019

(51) Int. Cl.
*G01N 33/24* (2006.01)
*G01N 27/12* (2006.01)
*E21B 49/02* (2006.01)
*E21B 49/08* (2006.01)
*G01N 27/07* (2006.01)
*E21B 43/26* (2006.01)

(52) U.S. Cl.
CPC .............. *G01N 33/24* (2013.01); *E21B 49/02* (2013.01); *E21B 49/086* (2013.01); *G01N 27/07* (2013.01); *G01N 27/122* (2013.01); *E21B 43/26* (2013.01)

(58) Field of Classification Search
CPC ...... G01N 33/24; G01N 27/07; G01N 27/122; E21B 49/02; E21B 49/086; E21B 43/26
See application file for complete search history.

(56) References Cited

U.S. PATENT DOCUMENTS

| 4,060,717 A | 11/1977 | Sitek |
| 9,529,112 B2 | 12/2016 | Qiu et al. |
| 2013/0342211 A1 | 12/2013 | Roy et al. |
| 2015/0293255 A1* | 10/2015 | Qiu ........................ G01N 33/24 324/339 |

(Continued)

FOREIGN PATENT DOCUMENTS

WO 2008016541 A1 2/2008

OTHER PUBLICATIONS

IC Controls, Conductivity Theory and Measurement, Technical Notes, Issue 4-1, available online at http://www.iccontrols.com/files/4-1.pdf (Year: 2005).*

(Continued)

*Primary Examiner* — Robert J Eom
(74) *Attorney, Agent, or Firm* — Trevor G. Grove

(57) ABSTRACT

In an embodiment a method is described which includes emplacing a sample within a measurement cell, wherein two or more electrodes are configured in the measurement cell; introducing a reactive fluid into the measurement cell; reacting the sample with the reactive fluid, wherein reacting the sample with the reactive fluid results in a change in an ion concentration in the reactive fluid; and measuring the resistivity of the reactive fluid using the two or more electrodes, wherein the resistivity is proportional to the ion concentration in the reactive fluid.

20 Claims, 5 Drawing Sheets

(56) References Cited

U.S. PATENT DOCUMENTS

2017/0074093 A1 3/2017 Adebayo et al.
2017/0146680 A1 5/2017 Boul et al.

OTHER PUBLICATIONS

Conway, Michael W., et al. "A comparative study of straight/gelled/emulsified hydrochloric acid diffusivity coefficient using diaphragm cell and rotating disk." SPE Annual Technical Conference and Exhibition. Society of Petroleum Engineers. (Year: 1999).*
Sarma, VV Jagannadha, and V. Bhaskara Rao. "Variation of electrical resistivity of river sands, calcite, and quartz powders with water content." Geophysics 27.4 (1962): 470-479. (Year: 1962).*
International Search Report and Written Opinion for corresponding International Application Serial No. PCT/US2019/025199, dated Jul. 17, 2019, 10 pages.

* cited by examiner

USING RESISTIVITY MEASUREMENTS TO MONITOR THE REACTION KINETICS BETWEEN ACIDS AND CARBONATE ROCKS

BACKGROUND

In the petroleum industry, downhole stimulation operations use chemical treatments to improve the rate and amount of oil production. For example, various mineral acids may be used in sandstone rocks to dissolve the rock and other solids, thereby providing a flow path for the formation fluid to flow through and be produced. For carbonate rocks, acids or chelating agents may be used to dissolve calcite during stimulation. Calcite reacts readily with acid and dissolves, enlarging pores and created channels that act as conduits for the formation fluid to flow through and be produced. The high reactivity of calcium carbonate to acids has made acidizing a common practice in carbonate reservoirs.

Although acidizing is common, the treatment process is monitored in a very limited sense. The most common parameters monitored during a chemical treatment include injection pressure, injection rate, downhole pressures, and distributed temperature, each of which may provide information related to the extent of the treatment. However, monitoring methods, such as temperature monitoring, may not be effective in every instance, which may result in poor zonal coverage following chemical treatment and reduced production rates in the production phase. The ability to assess treatment efficiency during stimulation operations to avoid poor zonal coverage and to optimize the efficiency of the chemicals injected based on the formation properties encountered at that injection site remains an important goal.

SUMMARY

This summary is provided to introduce a selection of concepts that are described further below in the detailed description. This summary is not intended to identify key or essential features of the claimed subject matter, nor is it intended to be used as an aid in limiting the scope of the claimed subject matter.

In an embodiment a method is described which includes emplacing a sample within a measurement cell, wherein two or more electrodes are configured in the measurement cell; introducing a reactive fluid into the measurement cell; reacting the sample with the reactive fluid, wherein reacting the sample with the reactive fluid results in a change in an ion concentration in the reactive fluid; and measuring the resistivity of the reactive fluid using the two or more electrodes, wherein the resistivity is proportional to the ion concentration in the reactive fluid.

In a further embodiment, a method is described which includes measuring a resistivity of a reactive fluid in contact with a reactive sample and monitoring changes in the resistivity of the reactive fluid as the reactive fluid reacts with the reactive sample.

Other aspects and advantages of the disclosure will be apparent from the following description and the appended claims.

DETAILED DESCRIPTION

Figure 1:
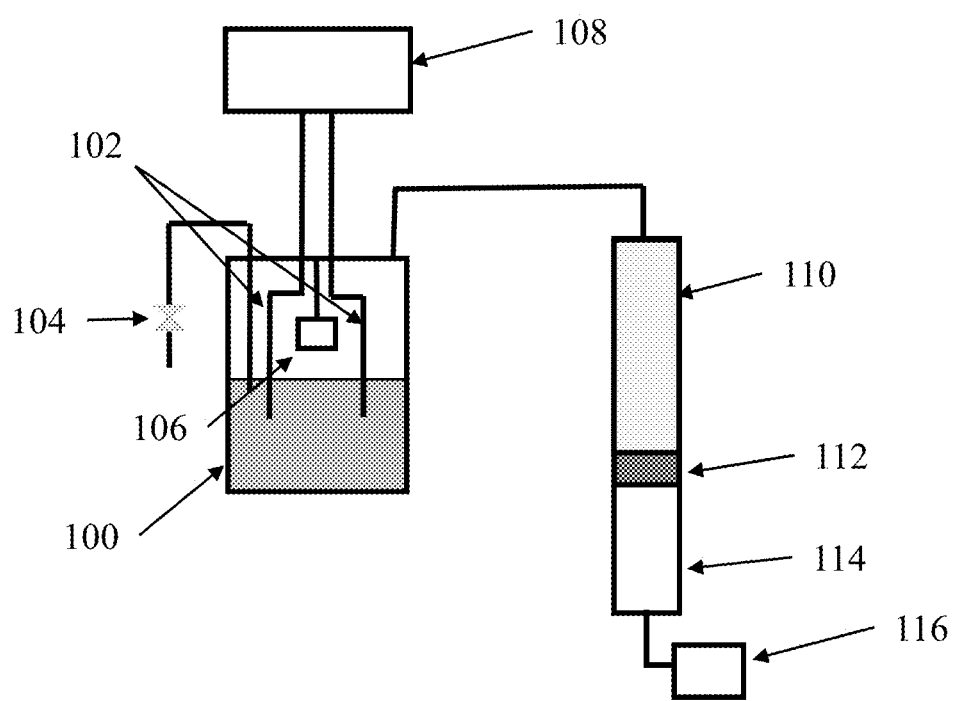
FIG. 1 is a schematic depicting a testing cell in accordance with embodiments of the present disclosure.

This disclosure relates generally to methods of determining reaction kinetics and diffusion phenomena in situ by measuring changes in the electrical properties of a solution in connection with chemical reactions that generate measurable changes in ion concentration. In one or more embodiments, the resistivity of a solution may be measured in real time, and used to measure reaction progression through changes of ion concentration. In some embodiments, methods in accordance with the present disclosure may be used to assay various stimulation treatments during completions design in reservoirs containing reactive rock. Methods in accordance with the present disclosure may also allow for the measurement of ion concentrations in real time and under reservoir conditions, including high pressure and high temperature (HPHT).

Determination of the diffusivity constant and reaction rates are an integral part of matrix stimulation job planning. The data are often used to populate field design models that allow engineers to predict the performance of stimulation treatments. However, laboratory procedures used to obtain these measurements are manual in nature, and require the effluent to be sampled at different stages of the acid reaction. However, sampling in such techniques may be hazardous to workers, increase operating costs, and may be sensitive to operator error that can create variations in result output.

Methods in accordance with the present disclosure may be used to study changes in conductivity of a reaction solution to investigate reaction kinetics and diffusion phenomena in situ. In one or more embodiments, methods may involve making distributed resistivity measurements within a controlled environment reaction cell.

In one or more embodiments, methods in accordance with the present disclosure may allow increased measurement speed and assaying larger numbers of stimulation compositions in order to optimize stimulation treatment design. In some embodiments, reaction kinetics determined from sample reactions may be used to determine the electrical properties of reacting fluids in varied conditions such as high pressure and high temperature (HPHT), which may be incorporated into various downhole stimulation models. For example, reaction kinetics may be used to predict wormhole and stimulation efficiency for treatment fluid compositions when injected downhole.

The dissolution of calcium carbonates such as calcite by an acid is an example of a reaction that generates measurable changes in free ion concentration that may be studied by methods of the present disclosure. The general formula for the calcium carbonate reaction with hydrochloric acid is given by Eq. 1.

$$CaCO_3 + 2HCl \rightarrow CaCl_2 + H_2O + CO_2 \qquad (1)$$

In the wellbore stimulation context, acids are injected downhole to increase formation porosity and fluid conductivity. The flux of acid over a reactive surface can be represented by Eq. 2, where J is the reaction rate in mole/cm$^2$·sec, $K_{mt}$ is the mass transfer coefficient in cm/sec, $C_b$ is the bulk acid concentration in mole/cm$^3$, and $C_s$ is the surface acid concentration in mole/cm$^3$.

$$J = K_{mt}(C_b - C_s) \tag{2}$$

Mass transfer coefficient $K_{mt}$ may be determined using a rotating disk reactor, in which a formation sample is rotated while exposed to a reactive solution (acid in this case). For a Newtonian fluid, $K_{mt}$ is given by Eq. 3, where v is kinematic viscosity (cm$^2$/sec), D is the diffusion coefficient (cm$^2$/sec), and ω is the rotation speed (rad/sec).

$$K_{mt} = 0.62 D^{2/3} v^{-1/6} \omega^{1/2} \tag{3}$$

At steady-state, the flux of H$^+$ ions at the surface of the sample is equal to twice the flux of Ca$^{2+}$ ions leaving the surface, as shown in Eq. 4.

$$J_{mt} = 2 J_{Ca^{2+}} \tag{4}$$

Therefore, during a rotating disk experiment, the hydrogen ion flux $J_{H^+}$ can be obtained by analyzing the Ca$^{2+}$ ion content in the solution. Combining Eq. 2 and 3, the reaction flux can be expressed as Eq. 5.

$$J_{H^+} = 1.62 D^{2/3} v^{-1/6} \omega^{1/2} (C_b - C_s) \tag{5}$$

In the domain of rotational speeds where the reaction is limited by mass transport, $C_s \ll C_b$, and Eq. 5 may be expressed in terms of flux of hydrogen in Eq. 6 or calcium ions in Eq. 7.

$$\frac{J_{H^+}}{0.62(v^{-1/6})C_b} = D^{2/3} \omega^{1/2} \tag{6}$$

$$\frac{J_{Ca^{2+}}}{0.31(v^{-1/6})C_b} = D^{2/3} \omega^{1/2} \tag{7}$$

Using these relationships, experiments may be performed using varied rotational speeds ω, while keeping all other parameters constant (i.e. temperature, acid concentration). Using the measured Ca$^{2+}$ and the above equation, a straight line can be produced by plotting Eq. 8 vs. $\omega^{1/2}$. The slope of the straight line will equal $D^{2/3}$, which may then be used to calculate diffusion coefficient D.

$$\frac{J_{Ca^{2+}}}{0.31(v^{-1/6})C_b} \tag{8}$$

For Non-Newtonian fluids, including emulsions, viscoelastic compositions, Pickering emulsions, and fluids containing solids such as particles and fibers, the viscosity may be given by Eq. 7, where K is the power law consistency index (gm/cm·s$^{(n-2)}$), n is the power law index, $\mu_a$ is the apparent fluid viscosity, and γ is the shear rate.

$$\mu_a = K \gamma^{n-1} \tag{9}$$

After solving the equation, the Reynolds and Schmidt numbers may be modified to take into account the shear dependence of the power-law viscosity. The modified Reynolds and Schmidt number may be given by Eqs. 10 and 11, where D is diffusivity (cm$^2$/s), N is K/ρ, cm$^2$/s$^{(n+2)}$, r is the radius of the disk (cm), and ρ is density (gm/cm$^3$).

$$Re = \frac{r^2 \omega^{2-n}}{N} \tag{10}$$

$$Sc = \frac{N \omega^{n-1}}{D} \tag{11}$$

Eq. 10 may then be used to define the Sherwood number (Sh) for the system given by Eq. 12, where φ(n) is a function that depends on power-law index n, $$Sh = \varphi(n) Sc^{1/3} Re^{1/3 \left[\frac{n+2}{n+1}\right]} \tag{12}$$

The average mass flux of a solute diffusing from bulk solution to the solid surface which is a function of the rotating speed (ω), bulk concentration (Cb), surface concentration (Cs), diffusivity (D), and power-law index parameters (n and K) may be written as Eq. 13, or equivalently as Eq. 14, where Jmt is the rate of mass transfer to a rotating disk (gmol/cm2·s) and kmt is the mass transfer coefficient for non-Newtonian fluids rotating at the surface of semi-infinite disk.

$$J_{mt} = \left[ \varphi(n) \left(\frac{K}{\rho}\right)^{-1/(3(n+1))} (r)^{(1-n)/3(n+1)} (\omega)^{1/(n+1)} D^{2/3} \right] (C_b - C_s) \tag{13}$$

$$J_{mt} = k_{mt}(C_b - C_s) \tag{14}$$

It is important to note that the mass flux, for non-Newtonian fluids, is proportional to the disk rotational speed raised to the power 1/(1+n). In case of Newtonian fluids, n equal to 1 and the rotational speed is raised to power 0.5.

The effect of diffusion coefficient on the kinetics of reaction is intrinsically hidden and its investigation requires the reaction to be measured experimentally. However, measurement of ions resulting from a reaction under study may be time consuming, requiring periodic sample collection from the reaction vessel, and sample analysis to determine ion concentration is done using analytical instruments such as atomic absorption spectroscopy or inductively coupled plasma. The above limitations can affect the overall time it takes to complete the measurements, in addition to limiting the total number of samples and measuring frequency.

In one or more embodiments, methods of the present disclosure may measure the changes in electrical properties of a sample fluid as the reaction progresses to study reaction rates and obtain diffusivity information. Electrical conductivity is a measure of the ability of a solution to conduct current. Current flow in liquids differs from that in metal conductors in that it must be carried by ions. Ions are formed when some chemicals such as salts are dissolved in a liquid to form electrical components having opposite electrical charges. For example, calcium chloride (reaction product of hydrochloric acid and calcite) generates Ca$^{+2}$ and Cl$^-$ ions when solubilized in an aqueous solvent. All ions present in the solutions contribute to the current flowing through the sample and therefore, contribute to the conductivity measurement. Electrical conductivity can therefore be used as a measure of the concentration of ionizable solutes present in the sample. Conductivity is typically reported as Siemens per meter (S/m), microSiemens per centimeter (μS/cm), or milliSiemens per centimeter (mS/cm).

In one or more embodiments, resistivity, the inverse of conductivity (1/conductivity), may be measured and converted to determine conductivity. Resistance is usually measured by injecting a known current through a sample and measuring the voltage drop across the sample. Using the Ohm's law the resistance, R, is given by Eq. 9, where V is voltage, and I is the electrical current.

$$R = \frac{V}{I} \tag{15}$$

However, the measured resistivity R from Eq. 15 is not an intrinsic property of a material, because resistivity also depends on the length of the sample and the cross sectional area experiencing current flow. The factors may be incorporated into an expression for R for a material shown in Eq. 16, where l is the length and s is the cross section of the material sample, and ρ is the material density.

$$R = \rho \frac{l}{s} \tag{16}$$

In some embodiments, l/s may be replaced by a cell constant, $K_{cell}$, referred to as cell constant to generate Eq. 17. The cell constant depends on cell geometry and may be determined by calibrating the particular setup using a known standard.

$$R = K_{cell} \rho \tag{17}$$

$K_{cell}$ can be determined empirically by measuring at least one sample with known resistivity. Using the above relationships, an expression for conductivity for a material in a measurement cell may be given by Eq. 18 below, where Conductivity is the temperature compensated reading, which may be given in Siemens/cm; $K_{cell}$ is the cell constant, which may be given in cm$^{-1}$, and may range from 0.01/cm to 50/cm in one embodiment; R is the measured resistance in Ohms, α is the temperature compensation factor as a percent change per ° C., which may be close to 2.0 in some embodiments, and T is the measured temperature of the sample in ° C.

$$\text{Conductivity} = \frac{K_{cell}}{R} \frac{1}{1 + \left(\frac{\alpha}{100}\right) * (T - 25)} \tag{18}$$

In one or more embodiments, a reaction cell may be assembled, as shown in FIG. 1. The reaction cell 100 may be constructed from a metal that resists corrosion and reaction with acid, such as HASTELLOY™, having a wall thickness sufficient to withstand the pressures encountered in the testing regime. A pump 116 is used to pump an inert fluid into accumulator 114. The accumulator 114 has a piston 112 that divides the space inside the accumulator into two compartments. The inert fluid pushes the piston 112, forcing the reactive fluid (or other fluid capable of reacting with the sample material) in the second compartment and into reaction cell 100.

The sample material to be assayed 106 is arranged within the interior volume of the cell 100 in the form of a disk as shown in FIG. 1 and attached to a rotating mechanism capable of rotating the disk at a user defined angular velocity. The resistance measuring electrodes 102 are configured within the interior volume of the cell and immersed in the reactive fluid contained in the interior volume of the cell 100 as shown in FIG. 1. The electrodes 102 are made of a material that is passive to the reactive fluid and does not corrode or cause side reactions. In some embodiments, electrodes 102 can be 1 cm by 1 cm squares and may be spaced at approximately 1 cm from each other. However, depending on relevant design considerations, electrodes may be of any dimension and separated at any distance from each other that preserves the ratio of electrode dimension and separation.

The circuitry of control module 108 may be used to inject current to the electrodes and measure the voltage drop across them. The orientation of the electrodes is such that during the reaction the fluid can easily enter the space between the electrodes and be measured and replaced with the new fluid as the reaction proceeds. Also shown in FIG. 1 is a sampling tube 104 which is used to take small samples of the liquid out of the cell for further measurements. The sampling tube 104 is used as quality control and is an optional feature.

Figure 2:
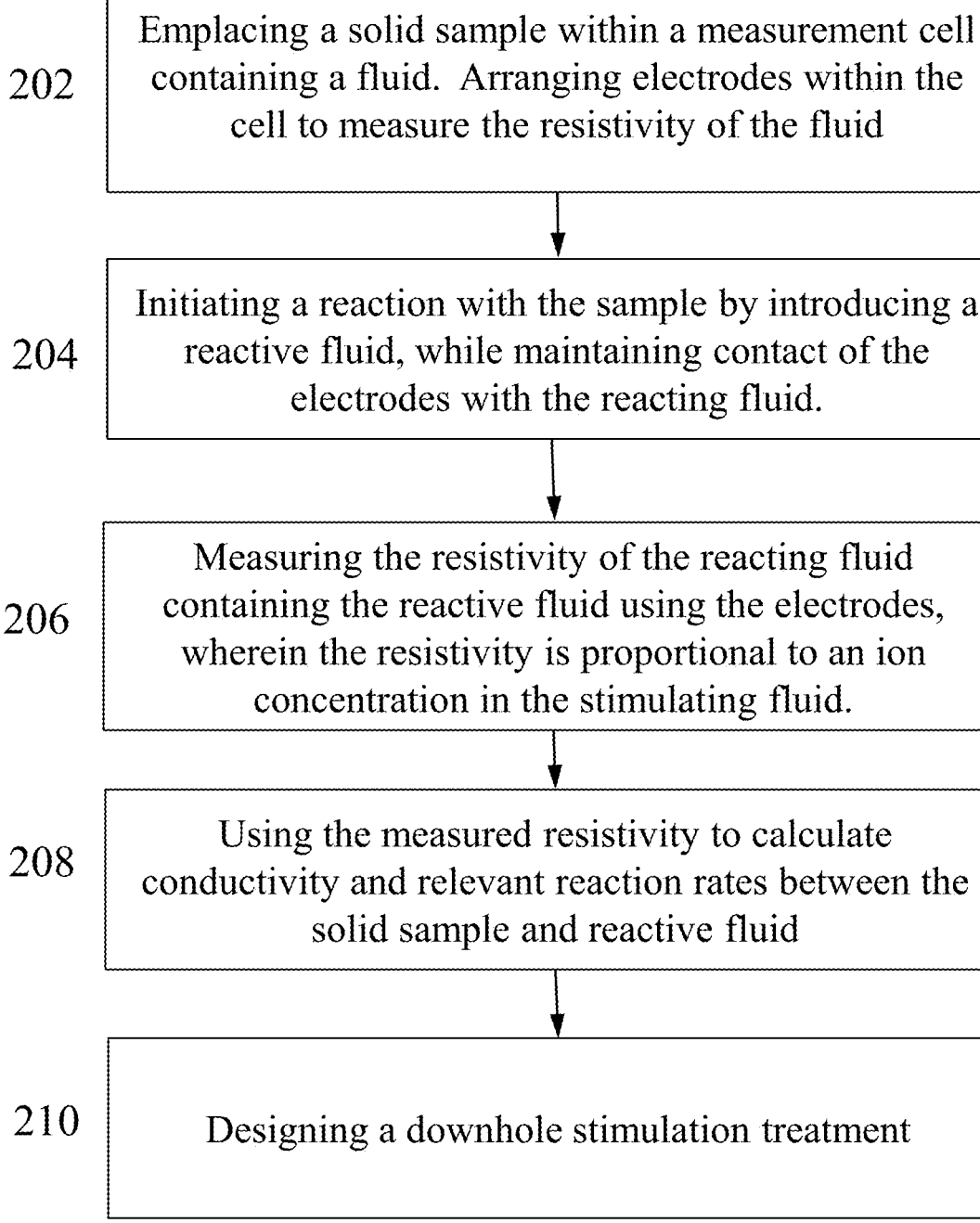
FIG. 2 is a flow diagram depicting a method in accordance with embodiments of the present disclosure.

With particular respect to FIG. 2, a flow diagram of a method in accordance with the present disclosure is shown. In one or more embodiments, methods may include assembling a cell, such as that described in FIG. 1, and emplacing a solid sample within the cell at 202. For wellbore stimulating applications, for example, the solid may be a reactive rock that is representative of a stimulation target formation. The solid may be placed in contact with a fluid in the cell that is being monitored by electrodes placed in contact with the fluid that maintains electrical contact between the electrodes. The reaction is initiated at 204 by introducing the reactive fluid, either in a single injection or metered over time. The electrodes maintain contact with the fluid in which the reaction is occurring (reactive fluid) to monitor the change in the resistivity.

At 206, resistivity may be converted to conductivity through known relationships and may be used to determine changes in ion concentration as the reaction progresses. Changes in ion concentration may also be used to determine kinetic information about the reaction between the solid sample and the reactive fluid at 208, such as one or more reaction rates or diffusion constants. Measurement techniques in accordance with the present disclosure may be done in real time during the reaction process and at the time scale of the acquisition rate, which may approach seconds in some embodiments, and fractions of a second (nanoseconds, microseconds, milliseconds, etc.) in other embodiments. In some embodiments, the impact of gas or other liquid solutes generated by a reaction on the local diffusivity close to and distant from the solid sample under test may be quantified as the reaction proceeds.

In some embodiments, multiple assays may be performed to screen various reactive fluid compositions (acid or chelating agent concentration, emulsion quality, temperature, pressure, etc.). Data obtained from screening methods may then be applied to the design of a stimulation treatment for downhole applications at 210.

In one or more embodiments, methods in accordance with the present disclosure may be conducted to measure the reaction kinetics of reactive rocks in response to exposure to various reactive fluids. Reactive rocks in accordance with the present disclosure include rocks that release ions in response to exposure to pH modification using acids and bases, or chelating agents. Reactive rocks may include carbonates, silicates, dolomite, sandstone, shales, and the like.

In one or more embodiments, methods in accordance with the present disclosure may be applied to study reactions and reaction kinetics in other contexts. In some embodiments, methods may be used to study wax or asphaltene appearance conditions by measuring the capacitance of the fluid at different locations throughout a reaction cell. These fluids could be reservoir crude samples or a mixture of reservoir crudes and chemicals specifically designed to either enhance or reduce the solids deposition in a crude oil stream.

In some embodiments, methods may be used to study the onset of foams and emulsions in reaction experiments. The electrical properties, including both conductivity and permittivity, vary with composition of the fluid, and in particular respond to different types of emulsions or foams. Changes in the electrical properties of the fluid composition may be useful for understanding the creation of emulsions and foams in a simulated downhole environment and developing a calibration curve that may be used to determine the quality of emulsion or foam once injected into or being produced from a wellbore.

Methods in accordance with the present disclosure may also be used to measure corrosion of solid samples, such as metals or alloys, which generate ions following reaction with a corrosive or reactive fluid. The concentration of these ions could be inverted using the general measurement principles described herein.

Reactive fluids may be selected based on the intended application and depending on the sample material that the fluid is being reacted with. In one or more embodiments, reactive fluids may include stimulating fluids that are used to remove or bypass formation damage by creating conductive channels or wormholes through a treated porous medium or formation. In one or more embodiments, prior to the initiation of a wellbore stimulation treatment, an operator may select a target reactive fluid for a particular porous medium or formation and, on the basis of this selection, conduct preliminary testing on a digital rock model of a porous medium or formation to determine an optimal reactive fluid for the application.

Reactive fluids in accordance with the present disclosure may include additional phases and rheological additives that modify the reactivity of the chemical component that interacts with the sample material, such as a reactive rock. In one or more embodiments, the reactive fluid may be an invert emulsion having an emulsified acid or acid source as an internal phase. Emulsified reactive fluids may include mixtures of acid sources and oleaginous (hydrophobic) fluids. In one or more embodiments, reactive fluids may also include the use of delayed acid sources having reduced reactivity such that the acid penetrates deeper into the formation before being spent.

In particular embodiments, delayed acid sources may include emulsified acids, acid precursors, or chelating agents. For example, an acid or other stimulating agent may be contained within the internal phase of an emulsion, preventing contact of the stimulating agent with the formation and allowing delivery of the stimulating agent further into the formation. In embodiments in which the stimulating agent is present within an aqueous phase, the external phase may be a hydrocarbon or other oleaginous phase such as oil or diesel. Other approaches may include the use of reactive foams, where, similar to the presence of an external phase, the presence of a gaseous phase in the foam acts as a barrier that prevents the reactive agent species from spreading into the formation. In some embodiments, the reactive fluid may be formulated as a diverting composition containing an acid source and a viscoelastic surfactant and/or a number of fluid loss additives. For example, diverting compositions may include mixtures of an acid source and cationic, anionic, or zwitterionic viscoelastic surfactants, mixtures of acid sources and various polymers. Acid sources may also be substituted or combined with chelating agents.

Acid sources in accordance with the present disclosure may include mineral acids such as hydrochloric acid, hydrofluoric acid, nitric acid, phosphoric acid and sulfuric acid, or organic acids such as formic acid, acetic acid, glycolic acid, citric acid and phosphonic acid. In some embodiments, reactive fluids may also include compounds that generate acids as a result of the dissolution of a solid acid source, or decomposition or hydrolysis, such as an acid produced from the hydrolysis of esters, amides, anhydrides, carbamates, urethanes, ureas, and the like.

In some embodiments, delayed acid sources may include acid precursors such as carboxylic acid esters that hydrolyze in response to downhole conditions, such as temperature and pH. In some embodiments, a hydrolyzable ester of C1 to C6 carboxylic acid and a C2 to C30 poly alcohol, including alkyl orthoesters, may be used. Carboxylic acid esters may include organic acid esters of a C2-C30 alcohol, which may be mono- or poly-hydric, such as an alkylene glycol mono-formate or diformate. Other delayed acid sources include those releasing C1-C6 carboxylic acids, including hydroxy-carboxylic acids formed by the hydrolysis of lactones, such as γ-lactone and δ-lactone, as well as alkoxycarboxylic acids. Delayed acid sources may also include polymerized acids that degrade in the presence of water to release free acids, including for example, and without limitation, polylactic acid (PLA), polyglycolic acid (PGA), carboxylic acid, lactide, glycolide, copolymers of PLA or PGA, and the like and combinations thereof. Delayed acid sources also include solid acid sources, such as dehydrated acid salts or solid organic acids. In some embodiments, non-limiting examples include fluoride sources which are effective for generating hydrofluoric acid include fluoroboric acid, ammonium fluoride, ammonium fluoride, and the like, solid organic acids including any listed above, and any mixtures thereof.

Chelating agents in accordance with the present disclosure may stimulate a formation by means of sequestering the metal components of the carbonate matrix. Possible chelants suitable for the described methods may include, for example, EDTA (ethylenediamine tetraacetic acid), diethylenetriaminepentaacetic acid (DTPA), citric acid, nitrilotriacetic acid (NTA), ethylene glycol-bis(2-aminoethyl)-N,N,N',N'-tetraacetic acid (EGTA), 1,2-bis(o-aminophenoxy) ethane-N,N,N',N'-tetraaceticacid (BAPTA), cyclohexanediaminetetraacetic acid (CDTA), triethylenetetraamine-hexaacetic acid (TTHA), N-(2-Hydroxyethyl)ethylenediamine-N,N',N'-triacetic acid (HEDTA), glutamic-N,N-diacetic acid (GLDA), ethylene-diamine tetra-methylene sulfonic acid (EDTMS), diethylene-triamine penta-methylene sulfonic acid (DETPMS), amino tri-methylene sulfonic acid (ATMS), ethylene-diamine tetra-methylene phosphonic acid (EDTMP), diethylene-triamine penta-methylene phosphonic acid (DETPMP), amino tri-methylene phosphonic acid (ATMP), and diethanolamine (DEA).

Reactive fluids may include an active stimulating component such as an acid source, delayed acid source, or chelating agent at various concentrations, for example at a percent by weight (wt %) in a range having a lower limit selected from 0.1 wt %, 1 wt %, 3 wt %, and 5 wt %, to an upper limit selected from 10 wt %, 25 wt %, 30 wt %, and 50 wt %, where any lower limit may range to any upper limit.

Reactive fluids in accordance with the present disclosure may include one or more wellbore fluid additives, particularly those used in the formation of wellbore completions and stimulation fluids. In one or more embodiments, reactive fluids may include fluid loss additives that include solids and/or fibers of various shapes and chemical properties that may plug thief zones and direct reactive components of the reactive fluids to less porous regions. For example, reactive fluids may contain solids having various shapes, sizes and rigidity, including, but not limited to, fibers, spheres, flakes, and irregular shapes to plug high permeability paths present in oil and gas reservoirs. High permeability paths may be naturally formed hydraulic fractures, dissolved channels or cavities in carbonate rocks, or large and connected interstices existing among the rock grains.

Fiber components and fluid loss additives that may be added to reactive fluids may include hydrophobic (or equivalently oleophilic) polymeric fibers that may be selected from, for example, polyolefins and polyaromatics that may include homopolymers, copolymers, and multiblock interpolymers of ethylene, tetrafluoroethylene, vinylidene fluoride, propylene, butene, 1-butene, 4-methyl-1-pentene, styrene, p-phenylene-2,6-benzobisoxazole, aramids, and the like. In other embodiments, the hydrophobic polymeric fibers may be selected from polyurethanes such as those formed from the reaction of diisocyanate and a polyol, polyester, polyether, or polycarbonate polyol. In some embodiments, fibers may be selected from hydrophilic fibers composed of polymers or co-polymers of esters, amides, or other similar materials. Examples include polyhydroxyalkanoates, polycaprolactones, polyhydroxybutyrates, polyethylene terephthalates, polytriphenylene terephthalate, polybutylene terephthalate, polyvinyl alcohols, polyacrylamide, partially hydrolyzed polyacrylamide, polyvinyl acetate, partially hydrolyzed polyvinyl acetate, and copolymers or higher order polymers (terpolymers, quaternary polymers, etc.) of these materials.

In some embodiments, the fiber component may be an acid soluble fiber that may include polyamides such as nylon 6, nylon 6,6, and combinations thereof. In other embodiments, hydrophilic fiber components may be at least one of polymers or co-polymers of esters that include, for example, substituted and unsubstituted polylactide, polyglycolide, polylactic acid, poly(lactic-co-glycolic acid), and polyglycolic acid, poly(ε-caprolactone), and combinations thereof. Suitable hydrophilic fibers may also be selected from celluloses and cellulose derivatives such as hydroxypropyl cellulose, hydroxyethyl cellulose, and carboxymethyl cellulose. Fibers may also include hydrophilic inorganic fibers that include glasses or acid soluble minerals such as calcium carbonate (e.g., calcite, vaterite, aragonite, limestone), magnesium carbonate (e.g., magnesite), calcium/magnesium carbonates (e.g., dolomite), calcium oxide, and magnesium oxide.

In one or more embodiments, reactive fluids may include particulates and weighting agents such as graphite, celluloses, micas, proppant materials such as sands or ceramic particles and combinations thereof. In other embodiments, particulate weighting agents may be selected from one or more of the materials including, for example, barium sulfate (barite), ilmenite, hematite or other iron ores, olivine, siderite, and strontium sulfate. In yet other embodiments, particulate weighting agents may be one or more selected from materials that dissolve in response to pH such as magnesium oxide, calcium carbonate (e.g., calcite, marble, aragonite), dolomite ($MgCO_3CaCO_3$), and the like.

Reactive fluids and modeled reactive fluids in accordance with the present disclosure may also include, without limitation, friction reducers, clay stabilizers, biocides, crosslinkers, gas generating agents, breakers, corrosion inhibitors, and/or proppant flowback control additives.

In the following examples, a cell was constructed as shown in FIG. 1. Samples of were assayed by contacting a sample of the formation with various concentrations of hydrochloric acid, measuring the conductivity of the acidic solution, and comparing the results with that expected using the OLI thermodynamic model. The OLI model is based upon published experimental data, and uses data regression wherever possible and estimation and extrapolation where required. This model provides general simulation capability giving accurate prediction for almost any water chemistry mixture. OLI provides rigorous predictive models and supporting data banking for electrical conductivity, viscosity and self-diffusivity over the full range of conditions. There is an offset between the two data sets which is due to the cell constant.

Figure 3:
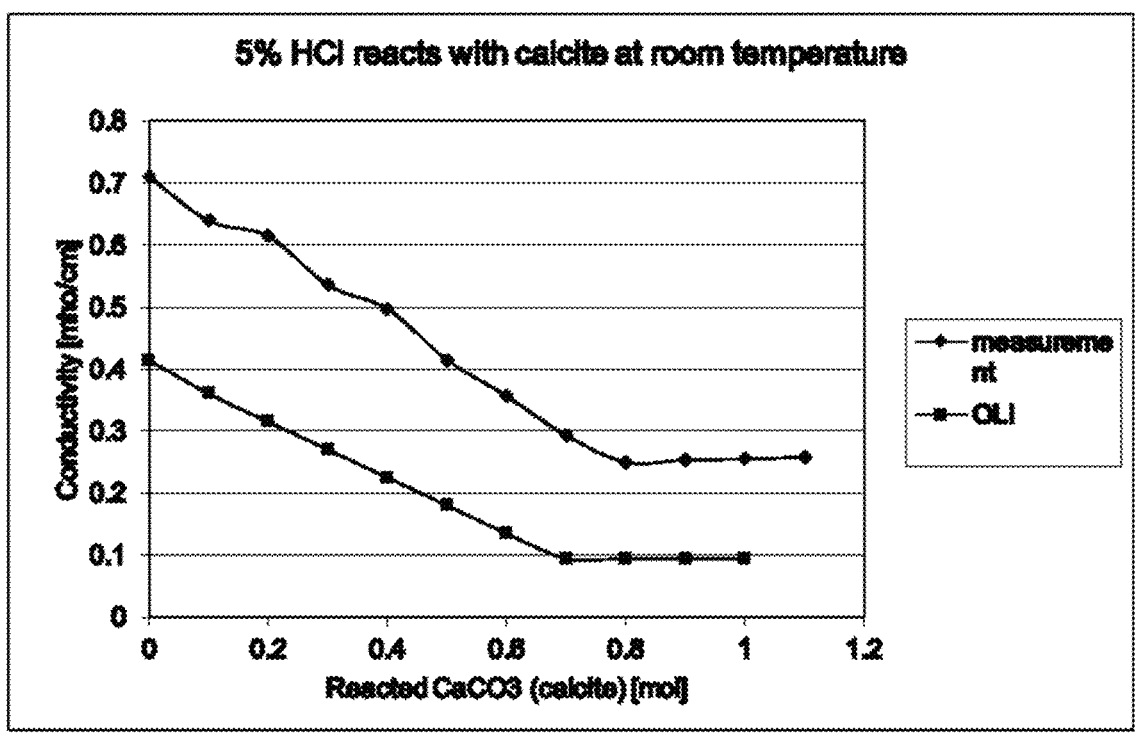
FIG. 3 is a graphical representation depicting conductivity as a function of reacted calcium carbonate for a reaction of 5% hydrochloric acid and calcite in accordance with an embodiment of the present disclosure.
Figure 4:
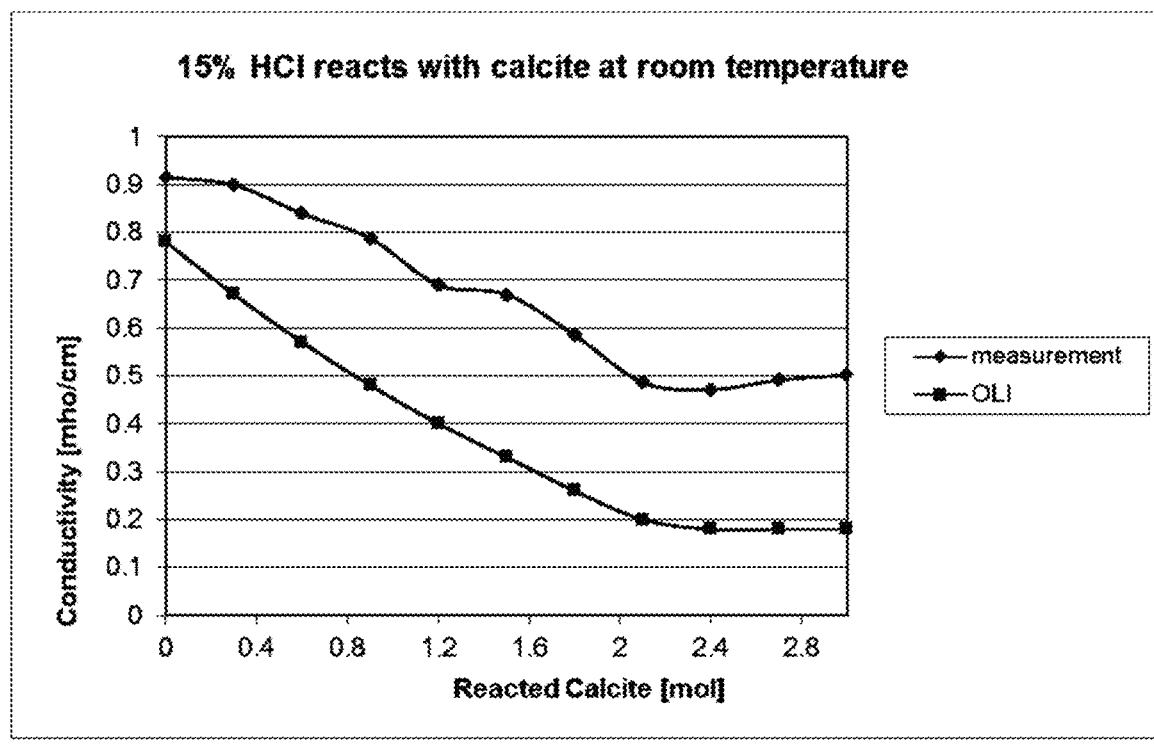
FIG. 4 is a graphical representation depicting conductivity as a function of reacted calcium carbonate for a reaction of 15% hydrochloric acid and calcite in accordance with an embodiment of the present disclosure.

The first experiment was conducted at the ambient conditions by reacting a pure sample of calcite with 5% hydrochloric acid. The resistivity is measured during the experiment and is shown in FIG. 3. Here, the model agrees with the data measured using conductivity. Another experiment was conducted under approximately the same conditions in which 15% HCl was reacted with pure calcite. The result is also compared with OLI as shown in FIG. 4, and shows good agreement with the predictive model.

Figure 5:
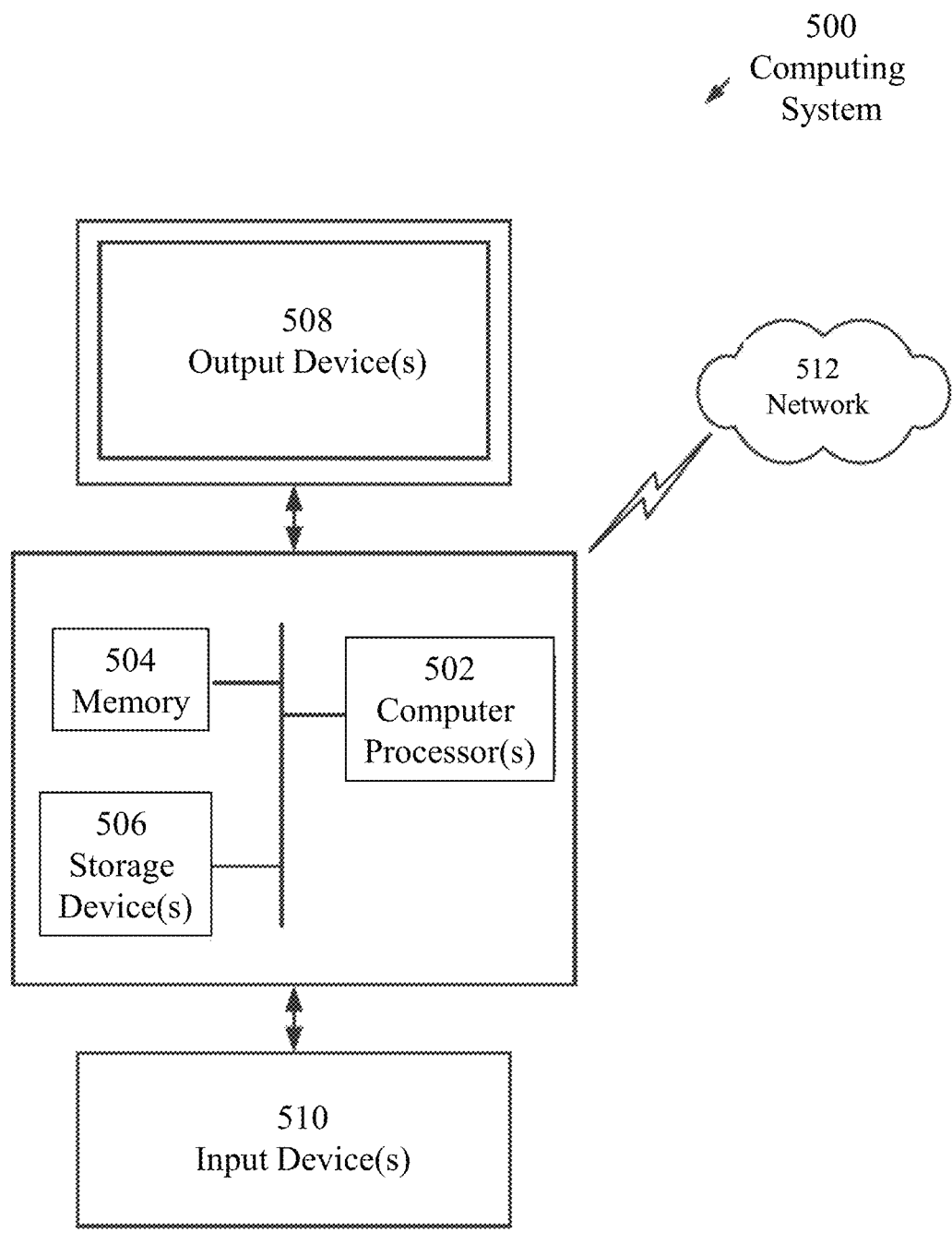
FIG. 5 is a schematic depicting a computer system in accordance with embodiments of the present disclosure.

Embodiments of the present disclosure may be implemented on a computing system. Any combination of mobile, desktop, server, embedded, or other types of hardware may be used. For example, as shown in FIG. 5, the computing system (500) may include one or more computer processor(s) (502), associated memory (504) (e.g., random access memory (RAM), cache memory, flash memory, etc.), one or more storage device(s) (506) (e.g., a hard disk, an optical drive such as a compact disk (CD) drive or digital versatile disk (DVD) drive, a flash memory stick, etc.), and numerous other elements and functionalities. The computer processor(s) (502) may be an integrated circuit for processing instructions. For example, the computer processor(s) may be one or more cores, or micro-cores of a processor. The computing system (500) may also include one or more input device(s) (510), such as a touchscreen, keyboard, mouse, microphone, touchpad, electronic pen, or any other type of input device. Further, the computing system (500) may include one or more output device(s) (508), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (500) may be connected to a network (512) (e.g., a local area network (LAN), a wide area network (WAN) such as the Internet, mobile network, or any other type of network) via a network interface connection (not shown). The input and output device(s) may be locally or remotely (e.g., via the network (512)) connected to the computer processor(s) (502), memory (504), and storage device(s) (506). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the disclosure.

Further, one or more elements of the aforementioned computing system (500) may be located at a remote location and connected to the other elements over a network (512). Further, embodiments of the disclosure may be implemented on a distributed system having a plurality of nodes, where each portion of the disclosure may be located on a different node within the distributed system. In one embodiment of the disclosure, the node corresponds to a distinct computing device. Alternatively, the node may correspond to a computer processor with associated physical memory. The node may alternatively correspond to a computer processor or micro-core of a computer processor with shared memory and/or resources.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method comprising:
   placing a rock sample within an interior volume of a measurement cell, wherein two or more electrodes are disposed in the interior volume of the measurement cell;
   introducing a reactive fluid into the interior volume of the measurement cell;
   reacting the rock sample with the reactive fluid in the interior volume of the measurement cell, wherein reacting the rock sample with the reactive fluid results in a change in an ion concentration in the reactive fluid in the interior volume of the measurement cell; and
   measuring resistivity of the reactive fluid in the interior volume of the measurement cell using the two or more electrodes, wherein the resistivity of the reactive fluid is dependent on reaction of the rock sample with the reactive fluid, and wherein the resistivity of the reactive fluid is proportional to the ion concentration in the reactive fluid.

2. The method of claim 1, further comprising: determining conductivity of the reactive fluid in the interior volume of the measurement cell using the measurement of resistivity of the reactive fluid in the interior volume of the measurement cell.

3. The method of claim 2, wherein:
   the conductivity of the reactive fluid in the interior volume of the measurement cell is determined according to the equation:

$$\text{Conductivity} = \frac{K_{cell}}{R} \frac{1}{1 + \left(\frac{\alpha}{100}\right) * (T - 25)}$$

where $K_{cell}$ is a cell constant, R is the resistivity of the reactive fluid in the interior volume of the measurement cell, $\alpha$ is a temperature compensation factor, and T is a measured temperature.

4. The method of claim 3, wherein $K_{cell}$ is in a range from 0.01/cm to 50/cm.

5. The method of claim 1, further comprising:
   monitoring the reaction between the rock sample and the reactive fluid and determining one or more reaction rates and/or diffusion constants.

6. The method of claim 5, further comprising:
   designing a downhole stimulation treatment using the one or more reaction rates and/or diffusion constants.

7. The method of claim 1, wherein the rock sample is configured on a device that rotates the rock sample at a user defined angular velocity.

8. The method of claim 1, wherein the reactive fluid is selected from a group consisting of: acid sources, delayed acid sources, chelating agents, and combinations thereof.

9. The method of claim 1, wherein the reactive fluid comprises a delayed acid source.

10. The method of claim 1, wherein the reactive fluid is selected from a group consisting of: viscoelastic surfactants and fluid loss additives.

11. The method of claim 1, further comprising:
    monitoring changes in the resistivity of the reactive fluid in the interior volume of the measurement cell as the reactive fluid reacts with the rock sample.

12. The method of claim 11, wherein the changes in the resistivity of the reactive fluid are monitored in real time.

13. The method of claim 11, further comprising:
    determining one or more reaction rates and/or diffusion constants from the changes in the resistivity of the reactive fluid.

14. The method of claim 13, further comprising:
    designing a downhole stimulation treatment from the one or more reaction rates and/or diffusion constants.

15. The method of claim 1, wherein placing the sample material within an interior volume of a measurement cell comprises arranging the sample material as a disk attached to a rotating mechanism.

16. The method of claim 15, wherein the rotating mechanism rotates the disk at a predefined angular velocity.

17. A method comprising:
    placing a sample material within an interior volume of a measurement cell, wherein two or more electrodes are disposed in the interior volume of the measurement cell, and wherein a reacting fluid is in the cell and maintains contact with the two or more electrodes;
    introducing a reactive fluid into the interior volume of the measurement cell;
    reacting the rock sample with the reactive fluid in the interior volume of the measurement cell, wherein reacting the rock sample with the reacting fluid results in release of ions from the rock sample causing a change in an ion concentration in the reacting fluid in the interior volume of the measurement cell due to release of the ions from the rock sample ; and
    measuring resistivity of the reacting fluid in the interior volume of the measurement cell using the two or more electrodes, wherein the resistivity of the reacting fluid is dependent on reaction of the rock sample with the reacting fluid, and wherein the resistivity of the reacting fluid is proportional to the ion concentration in the reacting fluid; and using the measured resistivity to calculate conductivity and relevant reaction rates between the sample material and reactive fluid.

18. The method of claim 17, wherein placing the sample material within an interior volume of a measurement cell comprises arranging the sample material as a disk attached to a rotating mechanism.

19. The method of claim 18, wherein the rotating mechanism rotates the disk at a predefined angular velocity.

20. The method of claim 19, wherein the sample material is a reactive rock, a metal, or an alloy.

* * * * *